United States Patent [19] [11] 4,053,635
Gorini et al. [45] Oct. 11, 1977

[54] SUBSTITUTED AMIDES OF 3-METHYL-4-PHENYL-3-BUTENOIC ACID, WITH A HIGH HYPOLIPEMIZING ACTIVITY

[75] Inventors: Sergio Gorini; Umberto Valcavi, both of Milan, Italy

[73] Assignee: Istituto Biochimico Italiano di Loredana Lorenzini S.a.s., Milan, Italy

[21] Appl. No.: 584,490
[22] Filed: June 6, 1975
[30] Foreign Application Priority Data
June 10, 1974 Italy ................................. 23797/74
[51] Int. Cl.² ................. C07C 103/76; A61K 31/165
[52] U.S. Cl. ........................... 424/324; 260/558 R; 542/438; 424/248.4
[58] Field of Search ............... 260/558 R, 247.7 H; 424/324

[56] References Cited
U.S. PATENT DOCUMENTS

| 2,937,117 | 5/1960 | Cottet et al. ..................... 424/317 |
| 3,231,469 | 1/1966 | Canonica ..................... 260/558 R X |
| 3,245,878 | 4/1966 | Berger et al. ................. 260/558 R X |
| 3,626,005 | 12/1971 | Scheben et al. ............. 260/558 R X |
| 3,780,102 | 12/1973 | Bayssat et al. ................... 260/558 R |
| 3,824,274 | 7/1974 | Franke et al. ............... 260/558 R X |
| 3,859,338 | 1/1975 | Engel et al. ................. 260/558 R X |

OTHER PUBLICATIONS
Mitsumori et al., CA 81:169330r (1974).
Valcavi, CA 81:77648x (1974).
Ohki et al., *Index Chemicus* 112906 (1969).

Buchi et al., J. Amer. Chem. Soc. 96 (17), pp. 5563-5565, (1974).

*Primary Examiner*—Daniel E. Wyman
*Assistant Examiner*—Thomas A. Waltz
*Attorney, Agent, or Firm*—Haseltine, Lake & Waters

[57] ABSTRACT

Amides of 3-methyl-4-phenyl-3-butenoic acid of the formula

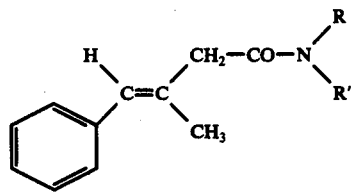

wherein R represents hydrogen, alkyl, hydroxyalkyl or cycloalkyl and R' represents alkyl, hydroxyalkyl or cycloalkyl, or R and R' together represent —CH$_2$—CH$_2$—O—CH$_2$—CH$_2$—, which are obtained by reacting the chloride of 3-methyl-4-phenyl-3-butenoic acid and amines of formula

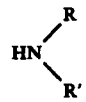

wherein R and R' have the above indicated meanings, having a high hypolipemizing activity.

2 Claims, No Drawings

SUBSTITUTED AMIDES OF 3-METHYL-4-PHENYL-3-BUTENOIC ACID, WITH A HIGH HYPOLIPEMIZING ACTIVITY

Former works had put in evidence that 3-methyl-4-phenyl-3-butenoic acid (I) and its amide (II) have interesting hypolipemic characteristics (U.S. Pat. No. 3,231,469, Jan. 25, 1966; L.Canonica et al. "Il farmaco" sch.edition, 14, 112, 1959; L.Canonica et al J.Biol.-Chem. 243, 1645, 1968)

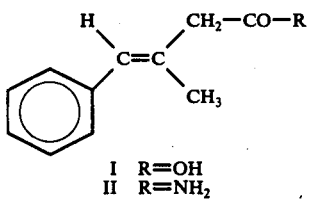

I R=OH
II R=NH$_2$

It is now found, surprisingly, that some substituted amides of formula IIIa–e, and particularly the diethylamide of 3-methyl-4-phenyl-3-butenoic acid (IIId),

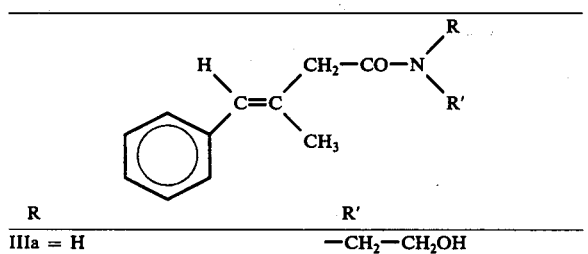

| | R | R' |
|---|---|---|
| IIIa = | H | —CH$_2$—CH$_2$OH |
| IIIb = | H | 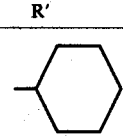 |
| IIIc = | —CH$_2$—CH$_2$—OH | —CH$_2$—CH$_2$—OH |
| IIId = | —CH$_2$—CH$_3$ | —CH$_2$—CH$_3$ |
| IIIe = | —CH$_2$—CH$_2$—O—CH$_2$—CH$_2$— | |

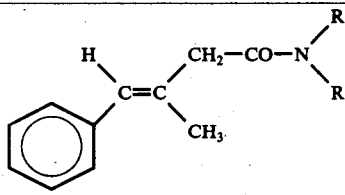

exhibit in numerous pharmacologycal tests a remarkably higher hypolipemizing activity than compounds I and II, and in some pharmocological tests a hypolipemizing activity higher than the ethyl ester of 2-(p-chlorophenoxy)-2-methyl propanoic acid (chlofibrate).

Furthermore products IIIa–e, and particularly diethylamide IIId, have a low toxicity in the test animal.

Products IIIa–e have been prepared by condensation of the chloride of 3-methyl-4-phenyl-3-butenoic and ethanolamine, cyclohexylamine, diethanolamine, diethylamine, morpholine.

TABLE I

LD 50 per os in the rat.

| Compound | mg/kg |
|---|---|
| IIIa | 1375 |
| IIIb | 3000 |
| IIIc | 1500 |
| IIId | 2300 |
| IIIe | 1000 |

TABLE II hypertriglyceridemia from Fructose*

| Treatment | | Triglyceridemia mg/100 ml ±SE | Significance against controls | Significance against animal set treated with Fructose |
|---|---|---|---|---|
| controls | | 41.7±1.7 | — | — |
| fructose | | 62.9±5.5 | p<0.01 | — |
| " | + I | 42.8±3.7 | not significant | p<0.02 |
| " | + chlofibrate | 42.2±5.4 | significant | p<0.05 |
| " | + IIIa | 62.9±6.4 | p = 0.01 | not significant |
| controls | | 45.6±4.7 | — | — |
| fructose | | 94.0±12.1 | p<0.01 | — |
| " | + I | 40.8±4.5 | not significant | p<0.01 |
| " | + chlofibrate | 48.9±2.4 | " | p<0.01 |
| " | + IIIb | 59.1±7.5 | " | p<0.05 |
| " | + IIIc | 69.6±3.9 | p<0.01 | not significant |
| controls | | 77.1±12.1 | — | — |
| fructose | | 155.2±19.2 | p<0.01 | — |
| " | + I | 100.8±13.8 | not significant | p<0.05 |
| " | + chlofibrate | 62.9±7.2 | " | p<0.01 |
| " | + IIId | 87.1±13.4 | " | p<0.02 |
| controls | | 45.3±4.5 | — | — |
| fructose | | 87.4±14.4 | p<0.02 | — |
| " | + I | 57.6±2.6 | p<0.05 | p<0.05 |
| " | + chlofibrate | 59.1±3.6 | p<0.05 | not significant |
| " | + IIIc | 61.1±5.1 | p<0.05 | " |

*Animal: Sprague-Dawley male rat, 150 g.; 6 rat sets. Treatment according to E. A. Nikkila et al., Life sci.5,89,1966; substances administered at the dose of 200 mg/kg day by gastric probing in two daily administrations for 5 days.

TABLE III

| Treatment | | Cholesterolemia mg/100 ml ± SE | Triglyceridemia° mg/100 ml ± ES | Hepatic Cholesterol° mg/g fresh tissue ± SE | Hepatic triglycerides mg/g fresh tissue ± SE |
|---|---|---|---|---|---|
| controls | (9) | 40.6±1.1($p<0.001$) | 65.1±2.3 ($p<0.01$) | 2.4±0.04 ($p<0.001$) | 3.8±0.3($p<0.001$) |
| hyperlipidic diet | (9) | 129.9±9.3 — | 117.3±17.7 — | 16.4±0.8 — | 56.4+3.8 — |
| idem + I | (6) | 142.4±7.7(not signif) | 91.5±13.6(not significat.) | 20.2±0.9(not signific.) | 37.7±5.6 ($p<0.02$) |
| idem + chlofibrate | (9) | 138.8±10.7 (" ") | 60.0±4.3 ($p<0.01$) | 18.5±1 (" ") | 30.3±2.5($p<0.001$) |
| idem + IIIb | (7) | 135.7±11.6 (" ") | 81.5±7.9(not significative) | 22.1±1.1 (" ") | 37.5±3.0($p<0.005$) |
| idem + IIId | (8) | 124.9±4.6 (" ") | 77.4±7.5 (" ") | 19.4±0.7 (" ") | 25.9±3.8 ($p<0.001$) |

°In parentheses, significativity towards the set treated only with diet.
*Animal: Sprague-Dawley male rat of the initial weight of 120 g (in parentheses the N. of animals).

Treatment: Hyperlipemia derived from hyperlipidic diet according to Nath N. et al., Nutrition J. 67, 289, 1959; the diet has been administered for 4 weeks. Each drug has been administered at the dose of 200/mg/kg/day per os for 4 weeks.

TABLE V

| Treatment | | g. alcohol drunk per rat | triglyceridemia mg/100 ml ± SE | Significance against controls | Significance against set treated with ethanol | cholesterolemia mg/100 ml |
|---|---|---|---|---|---|---|
| controls | (10) | — | 87±14 | — | — | 85±6 |
| ethanol | (8) | 16.1 | 238±44 | $p<0.01$ | — | 90±4 |
| " + chlofibrate 200 mg/kg | (7) | 20 | 183±29 | — | not signific. | 70±3 |
| " + IIId 200 mg/kg | (8) | 14.8 | 169±20 | — | " | 77±3 |
| " + IIId 300 mg/kg | (11) | 13.2 | 117±20 | — | $p<0.02$ | 81±3 |

*Animal Treatment:
Sprague-Dawley male rat of the average weight of 150 g. ethyl alcohol 10% in water for 1 week (in parenthesis, the N. of animals). The substances have been administered by gastric intubation at the dose of 200 and 300 mg/kg/day. In experiments of subchronic toxicity, the diethylamide of 3-methyl-4-phenyl-3-butenoic acid (IIId) has been administered per os at the doses of 150 mg/kg/day and of 300 mg/kg/day for 3 or 6 months: the product has been found fairly well tolerated.

TABLE IV

| Treatment | | Triglyceridemia mg/100 ml ± SE | Significance against controls | Significance against sets treated with ethanol |
|---|---|---|---|---|
| controls | (10) | 74.20±3.70 | — | — |
| ethanol | (10) | 135.80±13.30 | $p<0.001$ | — |
| idem + I | (9) | 275.11±31.63 | — | $p<0.001$ |
| idem + chlofibrate | (10) | 121.50±12.26 | — | not significant |
| idem + IIId | (9) | 90.0±14.83 | — | $p<0.05$ |

*Animal: Sprague-Dawley male rat of the average weight of 150 g. Treatment: 0.31 ml. ethanol in 4 ml. water twice a day (in parenthesis, the N. of animals) for 4 days. The substances have been provided by gastric intubation at the daily dose of 300 mg/kg.

EXAMPLE 1

Chloride of 3 methyl-4-phenyl-3-butenoic acid.

3 Kg of crystallized pure 3-methyl-4-phenyl-3-butenoic acid are dissolved into 3 l.benzene, 2,5 l of thionylchloride are added, and the mixture is kept 2 hours at 20° C and then taken slowly to 40° C and then refluxed 2 hours.

When the evolution of hydrochloric acid ceases, the excess thionyl chloride and benzene are evaporated under vacuum.

The residue is taken up twice with 2 liters of benzene and it is dry evaporated.

The chloride of 3-methyl-4-phenyl-3butenoic acid is distilled at 13-14 mm. of residual pressure at 118°-125° C: 307 g. chloride are obtained.

Monoethanolamide of 3-methyl-4-phenyl-3-butenoic acid (IIIa).

194 g of 3-methyl-4-phenyl-3-butenoic acid chloride (1 mole), dissolved into 500 ml benzene, are treated at −10° C with with 183 g of monoethanolamine (3 moles). The mixture is stirred at 20° C for 3 hours.

It is washed with water, 5% aqueous $NaHCO_3$ (to remove the chloride of the acid and the non reacted acid), and again with water to neutrality.

The benzene is evaporated under vacuum and the residue is crystallized three times from benzene.

There is obtained 257 g of monoethanolamide IIIa with m.p. 101°–103° C, carbon 71,20% (calculated 71.04%), hydrogen 7.81% (calculated 7.74%), nitrogen 6.38% (calculated 6.18%); $\zeta_{max}^{MeOH}$ 245-246 mμ ($E_{1cm}^{1\%}$ 714), I.R.nujol bands at 3300, 1650, 1550, 1340, 1310, 1280, 1210, 1180, 1080, 1060, 1040, 920, 870, 860, 850, 740, 730, 700 cm$^{-1}$.

Monocyclohexylamide of 3-methyl-4-phenyl-3-butenoic acid (IIIb).

95.2 g. of cyclohexylamine (0.96 moles) dissolved into 350 ml of anhydrous chloroform are treated at −15°/−20° C with 93.5 g. of chloride of 3-methyl-4-phenyl-3-butenoic acid(0,48 moles) dissolved into 125 ml chloroform during 1 hour at −15°/−20° C.

The mixture is stirred 2 hours at room temperature, and is then poured into a liter of iced water.

The chloroform is separated and is washed with 150 ml of aqueous 10% HCl, with 150 ml of aqueous 10% $NaHCO_3$, with 150 ml of water to neutral reaction. After evaporation from the solvent and crystallization from $CHCl_3$-ethyl ether, there is obtained 89 g. of monocyclohexylamide (IIIb) with m.p. 122°-123° C, $_{max}{}^{MeOH}$ 206 mµ ($E_{1cm}{}^{1\%}$ 848) mµ ($I_{1cm}{}^{1\%}$ 633), carbon 79.33 % (calculted 79.40%), hydrogen 9.01% (calculated 9.33%), nitrogen 5.44% (calculated 5.27%), I.R. nujol bands at 3250, 3090, 1660, 1630, 1570, 1350, 1280, 1260, 1250, 1220, 1170, 1100, 1080, 1020, 990, 920, 890, 770, 750, 730, 700 cm$^{-1}$.

Diethanolamide of 3-methyl-4-phenyl-3-butenoic acid (IIIc).

100 g. of diethanolamine dissolved into 350 ml of $CHCl_3$ are treated at −15°/−20° C within 1 hour with 93 g. of chloride of 3-methyl-4-phenyl-3-butenoic acid dissolved into 115 ml of $CHCl_3$.

The mixture is stirred 2 hours at +20° C, 200 ml $CHCl_3$ are added (to provide a complete solution), and the resulting mixture is poured into 1 liter of iced water.

The chloroform is separated, washed with 150 ml of 10% aqueous HCl with 150 ml, of 10% aqueous $NaHCO_3$ and with water to neutrality.

After drying over sodium sulphate and evaporating under vacuum, there is obtained 150 g. of diethanolamide (IIIc) having $\zeta_{max}{}^{MeOH}$ 245 mµ ($E_{1cm}{}^{1\%}$ 620), I.R. nujol bands at 3400, 3280, 1620, 1320, 1300, 1260, 1210, 1170, 1090, 1070, 1020, 950, 910, 880, 870, 860, 840, 810, 770, 750, 700 cm$^{-1}$.

Diethylamide of 3-methyl-4-phenyl-3-butenoic acid (IIId).

1.93 liters of diethylamine dissolved into 5.1 liters of $CHCl_3$ are treated at −10° C during 1 hour with 1.65 kg of chloride of 3-methyl-4-phenyl-3-butenoic acid dissolved into 2.25 liters of $CHCl_3$.

The mixture is then stirred while allowing the temperature to rise to 20° C, it is poured into 25 liters of water, separated.

The chloroformic phase is washed wit 8 liters 10% aqueous HCl, with 2 × 8 liters of water, with 8 liters of 10% aqueous NaOH, and with water to neutrality.

After drying over sodium sulphate, evaporating, diethylamide (IIId) is distilled at 0,5 mm, 134° - 136° C, and it is obtained kg 1,4 of product with $\zeta_{max}{}^{MeOH}$ 245 mµ($E_{1\ cm}{}^{1\%}$ 631), I.R. thin layer bands at 2980, 2970, 1640, 1470, 1430, 1380, 1360, 1320, 1260, 1220, 1140, 1100, 1070, 1030, 790, 740, 700 cm$^{-1}$.

Morpholide of 3-methyl-4-phenyl-3-butenoic acid (IIIe).

191,5 g of morpholine (2,2 moles) dissolved into 700 ml of $CHCl_3$ are treated at −20° C during 1 hour with the solution made from 194,5 g of chloride of 3-methyl-4-phenyl-3-butenoic acid in 250 ml of $CHCl_3$.

The temperature is allowed to rise to 20° C within 1 hour, the mixture is poured into 3 liters of water, is separated.

The chloroformic phase is washed with 1 liter 10% aqueous HCl, with 10% aqueous $NaHCO_3$, with water to neutral.

After drying over sodium sulphate, evaporating, the residue is taken up with ethyl ether.

Upon standing 4 days, big crystals of the product separate, is filtered, and washed with ether 78 g morpholide (IIIe) are obtained, with m.p. 49°-51° C, $\zeta_{max}{}^{MeOH}$ 245 mµ ($E_{1cm}{}^{1\%}$ 620), carbon 73.80% (calculated 73.43%), hydrogen 7.46% (calculated 7.80%), nitrogen 5.86% (calculated 5.71%).

We claim:

1. A method of treating hypolipemia in a hypolipemic patient which comprises administering to said patient an effective amount of the diethylamide of 3-methyl-4-phenyl-3-butenoic acid.

2. Diethylamide of 3-methyl-4-phenyl-3-butenoic acid.

* * * * *

UNITED STATES PATENT AND TRADEMARK OFFICE
CERTIFICATE OF CORRECTION

PATENT NO. : 4,053,635
DATED : October 11, 1977
INVENTOR(S) : GORINI ET AL.

It is certified that error appears in the above-identified patent and that said Letters Patent are hereby corrected as shown below:

| | | |
|---|---|---|
| Column 2, line 26 | | before "and" insert -- acid -- |
| Table I, | line 2 of column 2 | amend ">3000" to read -- 3000 -- |
| Table II, column 5, | line 14 | amend "P<0.05" to read -- $P \leq 0.05$ " |
| Table II, column 5, | line 16 | amend "P<0.02" to read -- $P \leq 0.02$ -- |
| Table II, column 2, | last line | amend "+ IIIc" to read -- + IIIe -- |
| Column 4, line 55 | | delete "with" (second occurrence) |
| Column 5, line 20 | | amend to read: -- $\lambda_{max}^{MeOH}$ 206 mµ ($E_{1cm}^{1\%}$ 848) and 245 mµ ($E_{1cm}^{1\%}$ 633), carbon -- |
| Column 6, line 11 | | amend "wit" to read -- with -- |

Signed and Sealed this

Twenty-second Day of August 1978

[SEAL]

Attest:

RUTH C. MASON
Attesting Officer

DONALD W. BANNER
Commissioner of Patents and Trademarks